United States Patent [19]
deWalle et al.

[11] Patent Number: 4,719,422
[45] Date of Patent: Jan. 12, 1988

[54] EDDY-CURRENT PROBES ESPECIALLY FOR THE SCANNING OF NON-FLAT PROFILED SURFACES

[75] Inventors: Stewart deWalle; Richard T. deWalle, both of Rexdale, Canada

[73] Assignee: Miep Holdings Inc., Rexdale, Canada

[21] Appl. No.: 879,513

[22] Filed: Jun. 27, 1986

Related U.S. Application Data

[60] Continuation of Ser. No. 736,059, May 20, 1985, abandoned, which is a division of Ser. No. 433,294, Oct. 7, 1982, Pat. No. 4,547,962.

[30] Foreign Application Priority Data

Oct. 9, 1981 [CA] Canada .................................. 387668

[51] Int. Cl.$^4$ .................... G01N 27/82; G01R 33/12; H01F 1/00
[52] U.S. Cl. .................................. 324/238; 324/234; 336/212
[58] Field of Search ................. 324/228, 234, 236–243; 336/211, 212

[56] References Cited

U.S. PATENT DOCUMENTS

| | | | |
|---|---|---|---|
| 2,265,136 | 12/1941 | Barnes et al. | 324/217 |
| 2,382,857 | 8/1945 | Camilli | 336/212 |
| 2,885,646 | 5/1959 | Bugg | 336/234 |
| 3,535,624 | 10/1970 | Wood | 324/220 |
| 4,101,832 | 7/1978 | Baker et al. | 324/238 |

Primary Examiner—Reinhard J. Eisenzopf
Assistant Examiner—Walter E. Snow
Attorney, Agent, or Firm—Rogers & Scott

[57] ABSTRACT

In a new method of manufacturing eddy-current probes, particularly such probes for the scanning of a test surface generated by a non-flat profile, a thin, flexible support layer is laid against the test surface so that it conforms exactly thereto. One or more tests coils have a sector thereof laid against the back face of the support layer so that the coil sector also conforms to the same profile in the plane of the coil and the profile. A plurality of separate ferrite core elememts are now laid inside the loop of the coil, or the loops of the coils, and pressed against the coil so as to form a core that also conforms to the profile to be scanned. The remainder of the coil (or coils) is pressed against the backs of the ferrite elements and the assembly is encapsulated to make it rigid enough for mounting in a test apparatus for scanning over the surface to be tested. The front face of the support layer is the "active" surface of the probe and conforms precisely with the profile, since it was generated thereby. The invention includes the probes made by the method.

6 Claims, 10 Drawing Figures

4,719,422

EDDY-CURRENT PROBES ESPECIALLY FOR THE SCANNING OF NON-FLAT PROFILED SURFACES

This is a continuation of application Ser. No. 06/736,059 filed May 20, 1985, now abandoned, which is a division of application Ser. No. 06/433,294 filed Oct. 7, 1982, now U.S. Pat. No. 4,547,962, issued Oct. 22, 1985.

FIELD OF THE INVENTION

The present invention is concerned with new eddy-current probes especially such probes intended for the scanning of non-flat profiled surfaces.

REVIEW OF THE PRIOR ART

Non-destructive testing of metal parts for the presence of flaws, pits, cracks, etc., by use of an eddy-current probe is now of course a well-established industry. Such probes consist for example of a solid cylindrical core of a ferrite material carrying a coil of wire; the impedance of the coil is monitored as the tip of the core is moved over the metal piece under test and flaws, etc. are detected by the change in coil impedance as the tip moves over the flaw. A typical size for such a core is about 1.5 mm diameter and the area over which it can detect a flaw is about 2 mm diameter, so that a large specimen must be scanned repeatedly if it is to be examined over its entire surface; such repeated scanning is of course a lengthy and tedious procedure, even when effected automatically by a machine.

One way in which the number of scans has been reduced is to use an assembly of a number of probes or coils which are moved together over the surface. However there is a practical limit to how close the probes can be packed and the operator accepts the risk that a flaw will be missed because it is small enough to be "scanned" by the space between the probes without affecting any of them. Another way is to make the probe larger, which involves the production of a larger core; this solution is in commercial practice only really suitable for specimens with flat surfaces. Thus, if the surface is not flat the core must be shaped accordingly, which limits its application to exactly similar specimens. Moreover ferrite is an expensive material that is difficult to machine, so that the probes become correspondingly costly.

DEFINITION OF THE INVENTION

It is therefore an object of the invention to provide a new method of making eddy-current probes.

It is a specific object to provide such a method that is particularly suitable for making probes for the scanning of non-flat profiled surfaces.

In accordance with the present invention there is provided an eddy-current probe having an active probe surface and for the scanning of a test surface, the probe active surface and the test surface having corresponding profiles in a plane which intercepts the test and probe surfaces so as to include the profiles, comprising:

a support member having parallel front and back surfaces with the said surfaces conforming in the said plane to the active probe and test surface profiles, a probe electrical test coil having a first portion thereof disposed immediately adjacent to the support member back surface and shaped to conform to said support member back surface and thus to the probe active surface and the test surface profiles in the said plane, and a probe core constituted by a plurality of separate ferrite core elements mounted inside the probe test coil immediately adjacent to one another and to the said first portion of the coil and conforming to the probe active profile and to the test surface profile in the said plane so as to constitute a unitary ferrite core shaped to the probe active profile.

DESCRIPTION OF THE DRAWINGS

Eddy-current probes that are particular preferred embodiments of the invention will now be described, by way of example, with reference to the accompanying diagrammatic drawings, wherein.

DESCRIPTION OF THE PREFERRED EMBODIMENTS

The application of the process and apparatus of the invention to the non-destructive testing of an airplane wheel has been selected to illustrate the invention, but is not intended in any way to limit the invention, which is of general application to the manufacture of eddy-current probes. Thus, the invention is particularly suitable for the production of probes intended for the scanning of surfaces that have been generated by a non-flat profile, but it is also suitable for the manufacture of probes intended for the scanning of flat profiles.

Aircraft wheels are subjected to regular non-destructive testing because of the high stresses to which they are subjected on take-off, landing and particularly taxiing. Under these conditions small flaws such as corrosion pits can lead quickly to the formation of hair-line cracks, which can then develop into major faults resulting for example in parts of the rim breaking away from the wheel. A wheel is a particular example of a shape that is generated by a profile, which in this case is rotated about a centre. Other articles can of course be generated as the result of a profile moving in some other mode, such as along a straight line.

Figure 2:
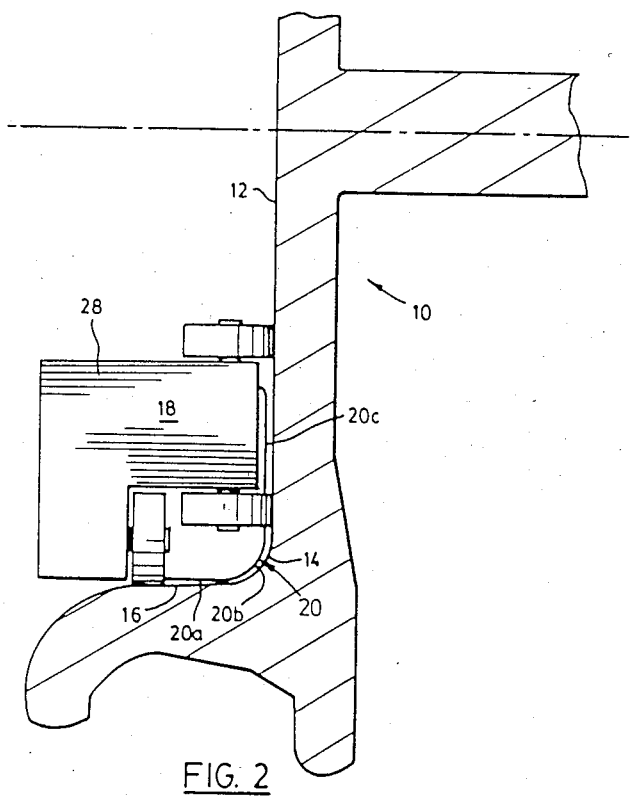
FIG. 2 is an enlarged plane cross-section view through the rim of a vehicle wheel to be tested on the apparatus of FIG. 1, and illustrating the use therein of a probe of the invention.

The profile in question is somewhat complex, as will be seen upon reference to the portion of a wheel section 10 shown in FIG. 2, consisting of a relatively long flat bead seat 12 that is connected by a concave bead seat radius 14 to a bead seat rim 16. The wheels of different aircraft types usually have different profiles. Fortunately it is only necessary in practice to examine the bead seat radius and the immediately adjoining portions of the bead seat 12 and bead seat rim 16, but this does require the use of a probe that can scan from the relatively flat bead seat 12 through the seat radius 14 and thence again to the lower part of the convex bead seat rim 16. Such scanning can be performed by a probe 18 of the invention having an active surface 20 that conforms to the bead seat radius and to the immediately adjoining parts 20a, 20b and 20c of the bead seat and bead seat rim.

Figure 1:
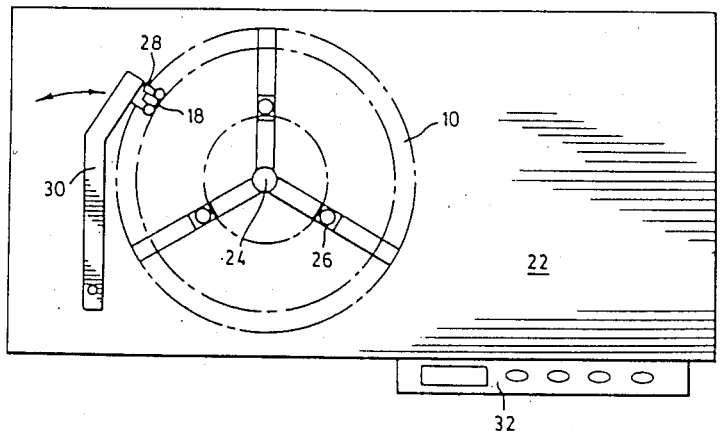
FIG. 1 is a plan view of an apparatus employing an eddy-current probe of the invention in the testing of a vehicle wheel for defects, such as an airplane wheel.

The test apparatus illustrated by FIG. 1 consists of a table 22 on which the wheel 10 can be mounted so as to be rotated about a vertical axis 24 by means of a clamp support structure 26 of any convenient form. The probe 18 is mounted in a wheeled carriage 28 which is in turn mounted on one end of a universally-movable articulated arm 30 that is spring-biased in any convenient manner to urge the wheeled carriage into engagement with the wheel periphery, so that the carriage will run freely on the wheel periphery, with the probe active surface in close proximity to the wheel surface, as the wheel is rotated about the axis. After each complete rotation of the wheel, or progressively as the wheel rotates, the probe is moved vertically by corresponding movement of the arm, so that the entire surface to be examined is scanned by the probe. The results of the scan are displayed and recorded by instruments on panel 32.

The exact construction of the test apparatus and the electrical equipment connected to the probe are not important to the description of this invention and are not further described.

Thus, the invention provides a relatively simple and inexpensive method of manufacturing a test probe having an active surface which in this embodiment is convex and conforms sufficiently accurately to the surfaces to be tested. Thus, the surface 20 has a central convex portion 20b that conforms to the bead seat radius and an end slightly convex portion 20a that conforms to the adjacent part of the bead seat rim sufficiently for the probe to be moved the necessary small amount up that part. The other end portion 20c is flat and the probe can therefore be moved along the relatively flat bead seat in order to scan it.

As can best be seen in FIGS. 5a–5d a probe of the invention is made by first applying a thin flexible support strip 34 to the profile to be tested, so that the length of the strip is parallel to the plane of the profile and so that the strip assumes the profile required for the probe active surface. The strip is simply laid in position on the test surface with its front face contacting the surface, and, if necessary, is tacked in position with a suitable adhesive to facilitate the subsequent steps of the process.

A flexible test coil 36 is formed, usually by pile winding a plurality of turns of the wire such that the required impedance is obtained, and then a portion of the coil of complementary shape to the strip 34 is laid against the back surface of the support strip in the said plane so that the portion also conforms to the profile of the test surface and the support strip 34. Conveniently during its winding adhesive is applied to the coil 36 to adhere the windings thereof together; if a slight excess is used this can be used to adhere the coil sector to the support member back surface.

In this particular embodiment a second test coil 38 of similar shape to the coil 36 is disposed parallel to the coil 36 but spaced therefrom to provide a balanced electrical circuit. This second coil 38 also has a complementary portion thereof laid against the back face of the support members so as to conform to the profile in a plane parallel to the plane of the coil 36.

Figure 3:
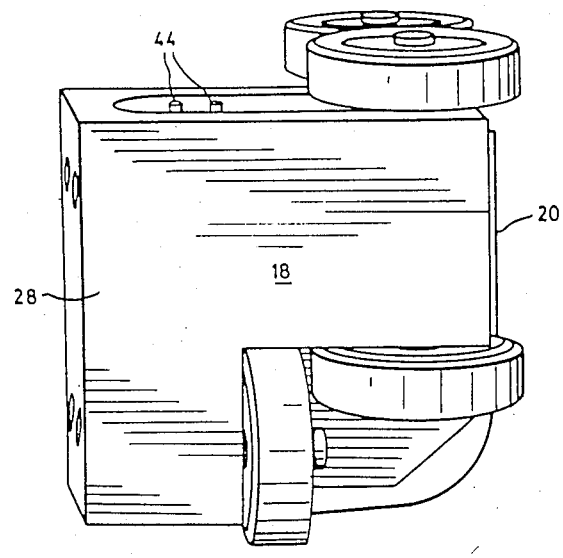
FIG. 3 is an enlarged perspective view showing a probe of the invention mounted in a carriage for use in the apparatus of FIG. 1.
Figure 4:
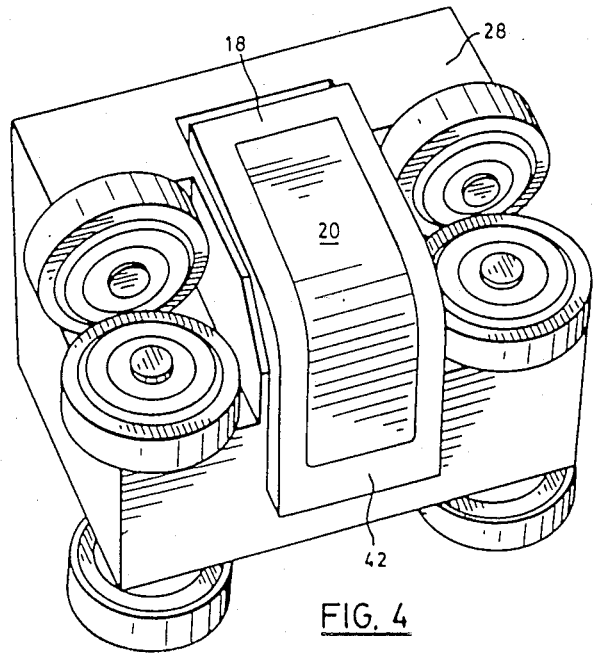
FIG. 4 is a perspective view showing the opposite side of the probe and carriage of FIG. 3, FIGS. 5a to 5d are cut-away progressive perspective views to illustrate the method of the invention.
Figure 5A:
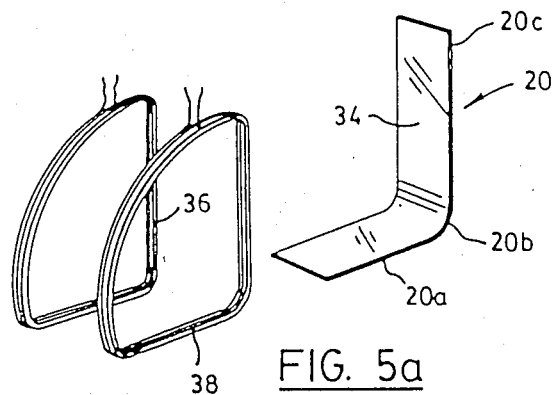
Figure 5B:
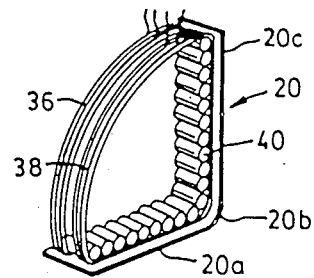
Figure 5C:
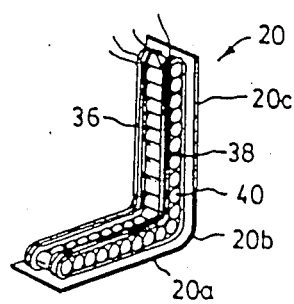
Figure 5D:
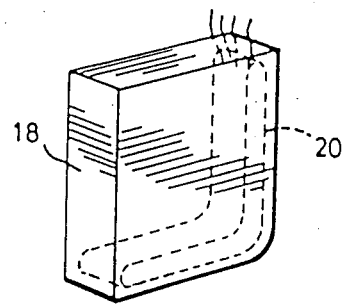

A plurality of separate narrow, elongated ferrite core elements 40 are now inserted within the loops of the coils 36 and 38 so as to extend through both coils transversely to the planes of the two coils, the cores being pressed against the portions adjacent the support member back surface so that together they form an effective electromagnetic ferrite core of shape conforming to the profile. The remaining portions of the coils are now pressed into close contact with the respective back portions of the core faces to give a laminated structure for maximum electromagnetic effect. As can best be seen in FIGS. 3 and 4 the rigid metal support frame 42 having terminals 44 for the coil ends and the interior open space filled with an encapsulating resin to hold the assembly firmly in place in the frame. When the resin has set the probe is removed from the surface and is ready for use, subject only to optional clean-up items such as removal of resin flash and polishing of the front active surface to ensure that it will move easily over the surface to be tested.

Since the active surface was formed into contact with the surface to be tested then it has an accurately formed complementary profile. Its mounting in the carriage will usually be such that it is spaced about 0.2 mm from the surface to be tested. Although in this embodiment a non-flat concave profile probe is described it will be apparent that the invention is also applicable to the manufacture of probes for use on convex or flat surfaces, in the latter case the invention providing an extended test surface reducing the number of scans to be employed, without the need for a costly and fragile specially formed unitary ferrite core.

In this particular embodiment the total length of the probe active surface was about 5 cm and the support layer was formed from a piece of polyester plastic tape of about 0.075 mm (0.003 in.) thickness. Each coil was wound to have an impedance of about 50 ohms at 70 kiloherz, the resulting coils having a cross-section perpendicular to the said plane that is 0.127 mm (0.005 in.) thick. The ferrite cores were of circular cross-section of 1.5 mm diameter (0.060 in.) and 6.35 mm (0.25 in.) length, the two coils being spaced about 1.60 mm (0.0625 in.) apart; twenty such cores were used placed with their circumferences touching their immediately adjacent cores.

Figure 7:
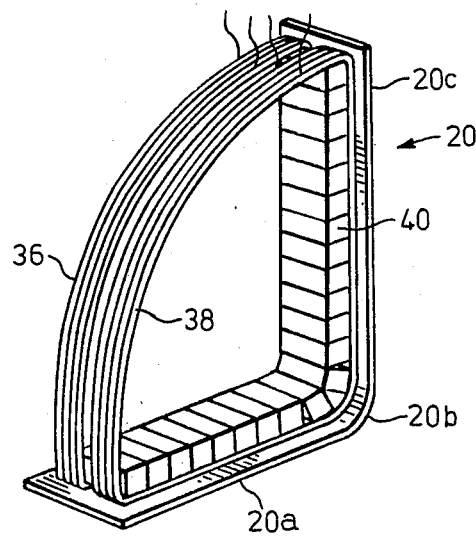
FIG. 7 is a cut-away perspective view corresponding to FIG. 5b of a second embodiment.

Although the cores employed in this embodiment are of circular cross-section, cores of other cross-sections can of course be used, as illustrated by FIG. 7, although the circular form has the advantage that the core peripheries can be made to touch one another for magnetic continuity and provide a relatively continuous-appearing surface irrespective of the complexity of the profile, and whether or not it includes convex and/or concave portions.

Figure 6:
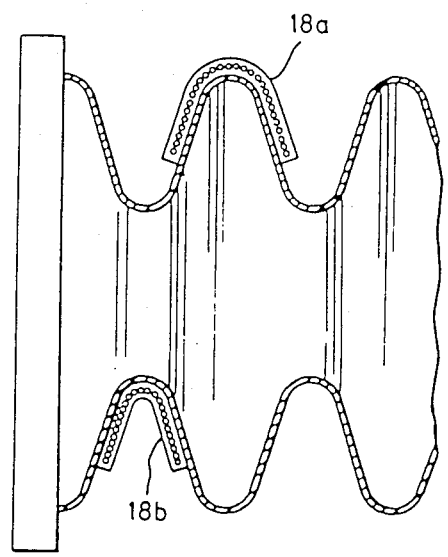
FIG. 6 is a cross-section through a bellows structure to be tested to show other applications of the invention.

FIG. 6 illustrates the complete flexibility of the invention in the manufacture of probes for differing shapes. Thus, one product requiring testing is metal bellows that in operation are subjected to pressure, mechanical flexing, temperature variations and the like, which can result in the development of cracks and consequent leakage. By the application of the invention it is possible to provide relatively easily and inexpensively and extremely concave-curved probe 18a and an extremely convex-curved probe 18b which together permit rapid inspection of the surface of the bellows. Each probe can have one or more coils, as is required for the test equipment to be employed and in each the ferrite cores can be of any suitable cross-section. The choice of core cross-section follows from the desire to provide the maximum amount of core inside the coils, and to this end various shapes can be employed and different shapes may be used at different parts of the same probe.

We claim:

1. An eddy-current probe having an active probe surface and for the scanning of a test surface, the probe active surface and the test surface having corresponding profiles in a plane which intercepts the test and probe surfaces so as to include the said corresponding profiles, the probe comprising:

a support member having parallel front and back surfaces with the said surfaces conforming in the said plane to the active probe and test surface profiles, a probe electrical test coil having a first portion thereof disposed immediately adjacent to the support member back surface and shaped to conform to said support member back surface and thus to the probe active surface and the test surface profiles in the said plane, and a probe core constituted by a plurality of separate narrow elongated ferrite core elements of circular or other cross-section mounted inside the probe test coil with their direction of elongation transverse to the plane of the coil, disposed with their longitudinal axes parallel to one another and perpendicular to the said plane of the coil, the elements being disposed immediately adjacent to one another and to the said first portion of the coil and conforming to the probe active profile and to the test surface profile in the said plane, so as together to constitute a unitary ferrite core shaped to the probe active profile.

2. An eddy-current probe as claimed in claim 1, wherein the ferrite core elements are of circular cross-section in the said plane and are disposed so that each element contacts its immediately adjacent element or two elements.

3. An eddy-current probe as claimed in claims 1 or 2, wherein at least the said first coil portion includes adhesive material adhering the first coil portion to the support member back surface and to the ferrite core elements.

4. An eddy-current probe as claimed in claims 1 or 2, wherein the support member, the test coil and the ferrite core elements are encapsulated to form a unitary body having an active probe surface conforming to the said profile.

5. An eddy-current probe as claimed in claims 1 or 2 including a second probe electrical test coil having a respective first portion thereof disposed parallel to and spaced from the said first portion of the first-mentioned coil so as to conform to the probe active surface profile in the respective plane, the plurality of ferrite core elements being mounted inside both of the said coils immediately adjacent to the respective first portions.

6. An eddy-current probe as claimed in claims 1 or 2, wherein the remaining portion of the test coil conforms in shape to the back surfaces of the ferrite core elements to sandwich said ferrite core elements between said first coil portion and the remaining coil portion.

* * * * *